United States Patent [19]

Reintjes et al.

[11] Patent Number: 5,275,168
[45] Date of Patent: Jan. 4, 1994

[54] TIME-GATED IMAGING THROUGH DENSE-SCATTERING MATERIALS USING STIMULATED RAMAN AMPLIFICATION

[75] Inventors: John F. Reintjes, Alexandria, Va.; Michael D. Duncan, Cheverly, Md.; Rita Mahon, Silver Spring, Md.; Lawrence L. Tankersley, Annapolis, Md.; Ronald W. Waynant, Laurel, Md.; Mark Bashkansky, Alexandria, Va.

[73] Assignee: The United States of America as represented by the Secretary of the Navy, Washington, D.C.

[21] Appl. No.: 861,213

[22] Filed: Mar. 31, 1992

[51] Int. Cl.$^5$ ............................................. A61B 6/00
[52] U.S. Cl. ..................................... 128/665; 128/633; 356/301
[58] Field of Search ..................... 128/664, 665, 633; 356/301

[56] References Cited

U.S. PATENT DOCUMENTS

| | | | |
|---|---|---|---|
| 4,178,079 | 12/1979 | Bjorklund et al. | 350/353 |
| 4,193,690 | 3/1980 | Levenson et al. | 356/301 |
| 4,495,949 | 1/1985 | Stoller | 128/665 |
| 4,648,714 | 3/1987 | Benner et al. | 128/665 |
| 4,832,035 | 5/1989 | Cho et al. | 128/633 |
| 4,945,239 | 7/1990 | Wist et al. | 250/358.1 |

Primary Examiner—Lee S. Cohen
Assistant Examiner—Brian L. Casler
Attorney, Agent, or Firm—Thomas E. McDonnell; George Jameson

[57] ABSTRACT

An apparatus for the time-gated optical examination of objects that are part of, embedded in or viewed through dense scattering materials is disclosed. In a preferred embodiment, the apparatus comprises: a light source for producing a first light pulse and a pump light pulse, each of the first and pump light pulses having a preselected pulse width at a preselected pump wavelength; a Raman generator for shifting the wavelength of the first light pulse to a preselected Stokes wavelength to form Stokes light; a first optical train for transmitting the Stokes light through the dense scattering material to obtain Stokes light comprised of a relatively small, image-bearing signal component including unscattered Stokes light or Stokes light with minimal deviation due to scattering, light followed in time by a relatively large amount of light scattered by the dense scattering material; a Raman amplifier; an optical system for transporting the Stokes light from the dense scattering material to the Raman amplifier; a variable delay path disposed between the light source and the Raman amplifier for varying the transit time of the pump pulse to cause the pump pulse to overlap in time with the signal component of Stokes light at the Raman amplifier, the Raman amplifier only amplifying the signal component of Stokes light that is overlapped in time by the pump pulse; and a two-dimensional detector for detecting the amplified signal component of Stokes light.

18 Claims, 3 Drawing Sheets

TIME-GATED IMAGING THROUGH DENSE-SCATTERING MATERIALS USING STIMULATED RAMAN AMPLIFICATION

BACKGROUND OF THE INVENTION

1. Field of the invention

The present invention relates to imaging devices and particularly to an apparatus and method for the time-gated optical examination of objects that are part of, embedded in or viewed through dense scattering materials using stimulated Raman scattering.

2. Description of the Prior Art

Images of objects that are part of, embedded in, or viewed through a medium in which a significant amount of multiple path scattering occurs are usually blurred or otherwise degraded in resolution or completely obscured because the different paths over which the scattered radiation travels causes the image to appear to arise from more- than one location within the scattering medium. There are several methods that can be used to overcome this problem, with each having certain disadvantages.

A first method involves the spatial filtering of the image to include only those rays that are not deviated too far from the axis of the optical system. The limitations of this first method occur because the spatial frequencies of the scattered radiation can overlap those required to form the image of the object. Either the resolution with which the object can be imaged is limited, or the scattered radiation cannot be filtered out effectively.

A second method of overcoming the blurring of the image is to time gate the transmitted signal so that only the earliest light that emerges from the scattering medium is recorded by a detector. This "first light" either is not scattered, or is scattered over a relatively short path compared to light that emerges later, and therefore provides the least amount of image degradation. The degree of improvement provided by this second method depends on the length of the scattering path over which the detected signal is integrated, which, in turn, is determined directly by the duration of the time gate. In general, the shorter the time gate, the better the image, down to some characteristic time that is determined by the scattering characteristics of the medium. Imaging through dense scattering materials, such as biological tissue, or solids or liquids that appear translucent or even opaque to the unaided eye can require gating times of the order of 10 picoseconds or less.

There are several techniques currently used to perform such time-gated imaging measurements, including various forms of electronic gating and optical gating. Electronic gating can be accomplished either by gating a photoelectric image tube directly, or by switching some other part of the photoelectric detection circuit. These techniques are currently limited to gating times of the order of 50-100 picoseconds (psec) or longer, corresponding to minimum scattering paths of the order of 1.5-3 centimeters (cm) by the limitations of available electronic switching devices.

Another technique involves the use of picosecond or femtosecond pulses for illumination of the object, followed by an optical gating technique to provide the time resolution. Such techniques can provide time gates in the picosecond or subpicosecond regime, depending on the length of the optical pulse. For comparison with electronic gating methods, a time gate of 100 femtoseconds corresponds to a scattering path of 0.003 cm.

One gating technique suitable for picosecond or femtosecond pulses is holography, in which the image is detected only by a coincidence between the illumination pulse and a reference pulse of the desired length. Conventional holography, in which the image is recorded on high resolution photographic film, requires a substantial amount of light in the transmitted signal to interfere with the reference pulse to establish the holographic record. It thus limits the extinction in the sample that can be accommodated. Electronic holography, in which the fringes are detected with a sensitive two-dimensional camera and the hologram is reconstructed through computer analysis, overcomes the sensitivity problem, allowing greater attenuation in the sample. However, all of the transmitted light is recorded at the detector. If a large fraction of the transmitted light is contained in the non-image bearing tail that is delayed through scattering, the interference fringes that form the hologram will be washed out, and the noise in the image will be increased until the image is totally obscured.

Holography can also be accomplished with broad-band, long-pulse laser light, in which the gate time is determined by the inverse of the bandwidth of the light. This approach provides subpicosecond gate times without the need for subpicosecond technology. However, as it has been applied to date, it suffers from the same disadvantages described above for picosecond holography: large signal requirements and relatively low contrast between the image-bearing portion of the transmitted light and the non-image-bearing tail.

Another technique for short pulse gating is the use of a Kerr shutter, in which the transmission of light through a cell between crossed polarizers is controlled by a second pulse of light. The gate times for this approach can be of the order of picoseconds, depending on the duration of the controlling light pulse and the response time of the active medium in the Kerr gate. This technique suffers from limitations in contrast because of leakage of the wrong polarization through the polarizers, and losses in the Kerr gate because the transmission is less than 100%. Contrast can be increased by cascading gates, but only at the expense of overall transmission. The loss of transmission can be especially detrimental for viewing through highly attenuating samples in which there is a limit on allowable irradiation levels, such as for living tissue.

Image amplification with picosecond time-gated amplifiers have also been described in the prior art. These amplifiers have been based on dye amplifiers pumped by picosecond laser pulses. By themselves the dye amplifiers have relaxation times of the order of several nanoseconds and, therefore, gating times of the same order of magnitude. Picosecond gating times were achieved by raising the dye concentration and pumping level to such a degree that substantial radiation from the upper laser level occurs, leading to population "dumping" and reduced lifetime of the upper state. The limitations of these amplifiers are that the high level of fluorescence necessary to produce the short gating time contributes a background on top of the amplified image, limiting the sensitivity and increasing the noise level. The amplifiers have had gains of only 100 to 1000, limiting the degree of contrast with the delayed light. Finally, fundamental considerations of the noise level of amplifiers show that the minimum noise level occurs when the time-bandwidth product $\Delta\nu\Delta t=1$. The dye fluorescence is radiated over the full bandwidth of the dye amplifier, of the order of 500 cm$^{-1}$. As a result, for gating times of the order of 10 picoseconds, the time-bandwidth product is in excess of 100, increasing the minimum noise value by the same factor.

Several other techniques are also possible. Streak cameras can be used to record the image. Time resolutions down to 2 picoseconds are currently possible. However, only a one-dimensional image is obtained, requiring scanning to produce a two-dimensional image. In addition, the streak cameras are of limited sensitivity, limiting their utility in detecting low-level signals. Another approach that uses time-gating involves the technique of four-wave mixing. In this approach the signal beam impinges on a non-linear medium that is being irradiated with co-propagating picosecond light pulses. Conversion of the signal light takes place only while the gating pulse is present. The main drawback to this approach is the combination of low conversion efficiencies associated with the conversion process (10% or less), coupled with limitations on the allowable illumination signal as set by the ANSI standards for irradiation of living tissue. Four-wave mixing using phase conjugation has also been suggested. The disadvantage of this technique is that, while phase conjugation can correct refractive distortion, it does not correct for scattering distortion due to fundamental considerations.

Non time-gating techniques also include the use of holographic recordings using spatial correlation to discriminate against the non image-bearing light. This approach has the same limitations due to low contrast with non-correlated light as discussed above for holography. Finally, use may be made of absorption in the sample to attenuate the longer paths associated with the multiple scattered light. This can work in materials that are highly absorbing, but not for materials that are primarily scattering rather than absorbing.

OBJECTS OF THE INVENTION

Accordingly, one object of the invention is to provide an apparatus and method for the optical examination of objects that are part of, embedded in or viewed through dense scattering materials with the us of time-gating.

Another object of the invention is to provide time-gated imaging of objects that are part of, embedded in or viewed through dense scattering media using stimulated Raman amplification.

Another object of the invention is to provide direct, two-dimensional imaging of objects that are part of, embedded in or viewed through dense scattering materials with a high degree of contrast of up to 10$^{10}$ with non-image bearing light, by using stimulated Raman amplification of image-bearing light.

Another object of the invention is to provide time-gated imaging of the interior of a scattering sample using stimulated Raman amplification.

A further object of the invention is to provide an apparatus and method for the direct time-gated imaging of biological tissue by using stimulated Raman amplification with picosecond time resolution.

SUMMARY OF THE INVENTION

These and other objects of the invention are achieved by providing a method and apparatus for the time-gated optical examination of objects that are part of, embedded in or viewed through dense scattering materials using stimulated Raman scattering.

BRIEF DESCRIPTION OF THE DRAWINGS

These and other objects, features and advantages of the invention, as well as the invention itself, will become better understood by reference to the following detailed description when considered in connection with the accompanying drawings wherein like reference numerals designate identical or corresponding parts throughout the several views and wherein.

DETAILED DESCRIPTION OF THE PREFERRED EMBODIMENTS

Before the drawings are discussed, it should be noted that the invention overcomes the limitations of the various prior art methods discussed above by providing an apparatus that acts as an optical shutter with an open time that can be as short as a few picoseconds or less, and also provides gain up to 10$^{10}$ to minimize the illumination intensity required, or alternatively to allow viewing through samples or objects that have very high levels of attenuation. It provides a direct two-dimensional image and a high degree of contrast (up to 10$^{10}$) with non image-bearing light.

Figure 1:
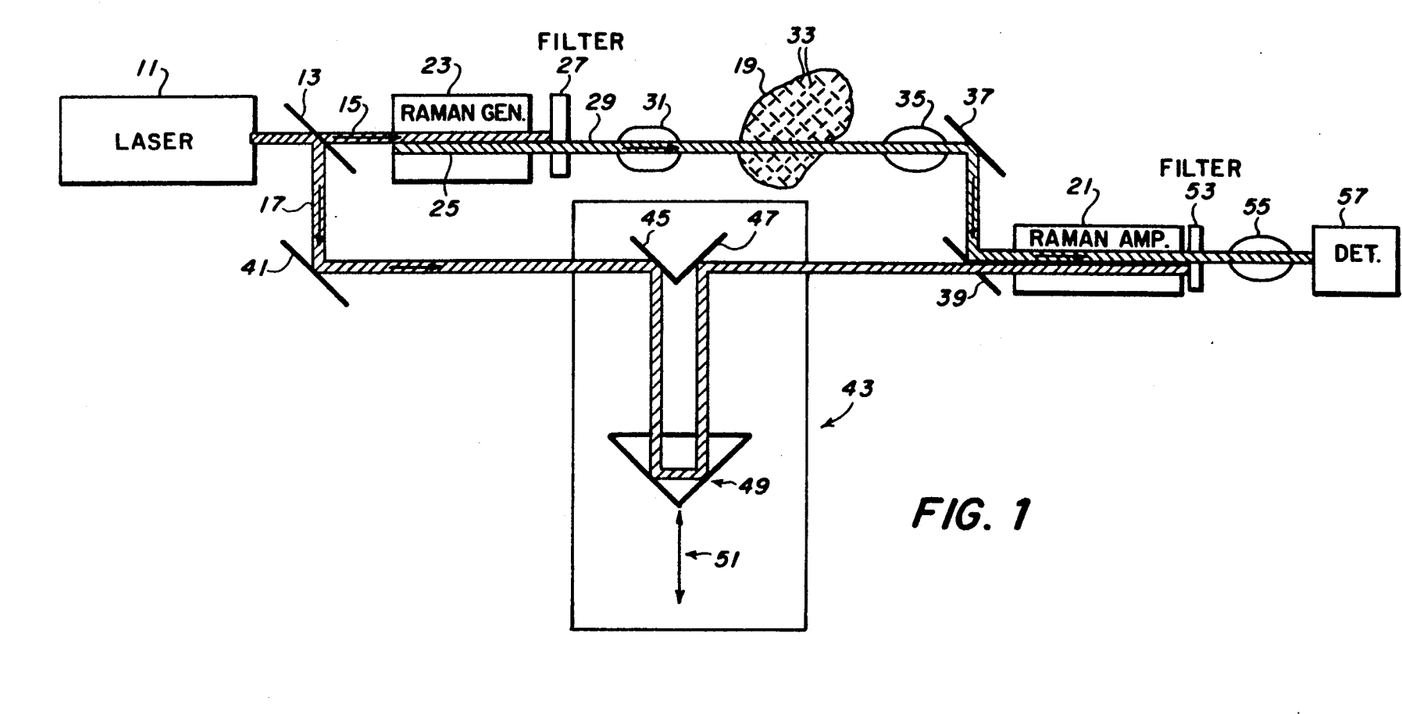
FIG. 1 illustrates a first embodiment of the invention.

Referring now to the drawings, FIG. 1 shows a first embodiment of the invention. A laser 11 or other source of coherent light produces light pulses at an exemplary 1 KHz (kilohertz) rate, each pulse having a suitable pulse width or duration of, for example, between 1 and 20 picoseconds (psec) at a Raman pump wavelength $\lambda_p$ (to be explained). Each light pulse from the laser 11 is divided by a beamsplitter 13 into two light pulses, which respectively propagate along separate paths 15 and 17. The light pulse in path 15 subsequently causes the generation of a signal pulse to illuminate a sample or object 19 that is to be optically examined (to be explained), and the light pulse in path 17 is a pump pulse which is subsequently used for pumping a time-gated amplifier 21 (to be explained). The structural elements along path 15 will be described before the structural elements along path 17.

The light pulse that is transmitted through the beam splitter 13 into path 15 enters a Raman generator 23 which contains a Raman material (not shown). In response to the interaction of the Raman material with this light pulse, the Raman generator 23 produces a pulse of light that is shifted in wavelength from the wavelength of the light pulse produced by laser 11 by a frequency corresponding to the Raman shift of the material contained in Raman generator 23. This light pulse, which has a Raman-shifted wavelength $\lambda_s$, is called Stokes light and propagates along path 25.

The Raman material in the Raman generator 23 can be a gas, a liquid or even a solid. Typically, a Raman generator is filled with a gas, such as hydrogen or methane, under a predetermined gas pressure. Each different type of Raman material produces a different, associated Raman-shifted wavelength.

Depending on the particular needs of the system of FIG. 1, the Raman generator 23 can be a single pass Raman generator, a multiple pass Raman generator cell or a Raman generator-amplifier. It can also comprise an independent laser. If this is the case, the two wavelengths, $\lambda_p$ and $\lambda_s$, must obey the relationship $(1/\lambda_p)-(1/\lambda_s)=\tilde{\nu}_o$, where $\tilde{\nu}_o$ is the Raman shift of the material used in the Raman amplifier 21.

The Stokes-shifted light pulse in path 25 and the unconverted light pulse in path 15 pass to a filter 27 which transmits the Stokes-shifted light at the desired Stokes wavelength $\lambda_s$ therethrough and into path pulse at the laser wavelength $\lambda_p$ in path 15. The Stokes-shifted light pulse propagates along path 29, and passes through an optical train 31 and onto the sample or object 19 that is to be optically examined. The optical train 31 can be comprised of one or more lenses (not shown), one or more mirrors (not shown), a fiber bundle (not shown), or a combination of these components, arranged to adjust the spatial size of the Stokes-shifted light beam that was produced in the Raman generator 23, so that it provides the desired illumination area at the sample 19. The optical train 31 can also contain filters (not shown) that can be used to adjust the intensity of the light produced by the Stokes generator 23 in order to meet any maximum illumination requirements that sample 19 may have.

It should be noted at this time that the light entering the sample 19 should preferably be collimated. The Stokes-shifted light propagating out of the Stokes generator 23 should preferably be collimated. However, in the event that the Stokes-shifted light is not collimated at the output of the Stokes generator 23, the optical train 31 should preferably be designed to collimate this light also.

The sample 19, which is typically a dense scattering material, is shown in FIG. 1 with a plurality of little lines 33 representing little scattering pieces due to the internal structure of the material in the sample 19. The light that is ultimately going to form the signal light for the Raman amplifier 21 is the light that is transmitted through this material in the sample 19 in the least time. More specifically, this signal light is that small portion of the light emerging from the sample 19 that has either not been scattered within the sample 19 or has been scattered with minimal deviation from its original path. Thus, this signal light is that small portion of the light that comes out of the sample 19 first and in the least time.

The nature of this signal light that has been transmitted through the sample 19 without scattering or with minimal scatter depends on the thickness and nature of the material of the sample 19. Depending on the type of sample 19, this non-scattered signal light can be attenuated by $10^{14}$ or even more in passing through the sample 19. It is believed that such attenuations would be typical of the anticipated loss of light in being transmitted through about 4 centimeters of tissue, such as the human breast. It should be noted at this time that, when the sample 19 is live human tissue, such as the human breast, the passage of optical radiation through such human tissue will not cause any damage to that human tissue as long as the intensity of the light impinging on that human tissue is below the limit for skin damage. In contrast, examination of the breast with x-rays, as is currently done in mammography, can cause damage due to the ionizing nature of the radiation.

In addition to the signal light that has been transmitted through the sample 19 without being scattered, there will be light that emerges from the sample 19 after it has been scattered. This light will have been scattered over various paths (not shown) throughout the scattering material of the sample 19. It will have been scattered and spread laterally to the sides of the unscattered light. As a result, most of such scattered light will be delayed in time. However, there may be some component of this scattered light that is dominantly forward scattered such that it may also contribute to the image in the unscattered signal light.

The bulk of the scattered light that passes through the sample 19 will consist of light that has been sufficiently, multiply scattered that it no longer contains any image characteristics. It will be just diffused light and all of the image information of the structure of the sample 19 will have been lost. This scattered light without any image characteristics comprises most of the optical energy of the light pulse that was transmitted to the sample 19. The exact ratio between the delayed or trailing scattered light and the leading image-bearing signal light depends on characteristics of the sample 19. Exact values of this ratio are not known, but it can easily be many orders of magnitude greater than unity.

The next objective of the invention is to find that small signal light portion of light in front that carries the image of interest from or through sample 19 in the presence of the large amount of light without an image that is following along right behind the image-bearing portion of light. The light following behind the image-bearing signal light is spread out in time. This spread in time may extend from several picoseconds to hundreds of picoseconds or even to nanoseconds. Thus, the bulk of the light energy that is transmitted through the sample 19 would be carried in a long scattered tail that could be spread out in time by a factor of 10–1000.

The total light emerging from the sample 19, which is comprised of unscattered signal light and scattered light portions, propagates through an optical imaging train 35, reflects from mirror 37, and reflects from dichroic beam splitter 39 into the Raman amplifier 21. The optical imaging train 35 is comprised of a sequence of two or more imaging elements, such as lenses and/or spherical mirrors (not shown), that relay the image of sample 19, or a plane within the sample 19, into the Raman amplifier 21. The optical train 35 can be comprised of one or more lenses (not shown), one or more mirrors (not shown), a fiber bundle (not shown), or a combination of these components.

Preferably the optical train 35 includes two lenses (not shown) for relaying the image. The first lens is placed one focal distance away from the plane in sample 19 that is to be imaged. The other lens is separated by the sum of its focal length and the focal length of the first lens from the first lens. In relaying the image, the first lens essentially creates a Fourier transform of the image in its own focal plane (not shown), and the second lens creates a Fourier transform of that first transform, effectively performing a double Fourier transform to retrieve and apply the original image of the sample 19 to the Raman amplifier 21. The advantage of the optical train 35 performing a double Fourier transform over it performing a simple imaging operation is that the double Fourier transform operation not only relays the image to the Raman amplifier 21, but it also reconstructs the original preferably collimated beam in the amplifier 21. In this manner the rays of the image are more completely contained within the amplifier 21 so that they can have the full interaction along the length of the Raman amplifier 21 (to be discussed).

Mirror 37 controls the path of the transmitted light from the optical imaging train 35 and in conjunction with the dichroic beamsplitter 39, directs that transmitted light into the Raman amplifier 21. Dichroic beamsplitter 39 reflects the Stokes beam from mirror 37 directly into Raman amplifier 21.

Up to this point in this discussion of FIG. 1, the structural elements along path 15 have been discussed. It should be noted at this time that, while the light pulse in path 15 has been propagating through the Raman generator 23 and the resultant Stokes beam through the sample 19, the pump pulse in path 17 has been propagating along a somewhat parallel path. This pump pulse in path 17 is at the Raman pump wavelength $\lambda_p$. The structural elements along path 17 will now be discussed.

As shown in FIG. 1, the pump pulse in path 17 is reflected from mirror 41 into optical delay line 43. The optical delay line 43 is comprised of mirrors 45 and 47 and a retroreflector or rooftop prism 49 that is translatable in the directions of double arrows 51. Thus, the rooftop prism 49 can be translated in either of the two directions shown by arrows 51. Typically, the rooftop prism 49 is mounted on a translatable stage (not shown) that is moved by a translation means (not shown), such as a screw or an electric motor. The translation means causes the translatable stage to move the rooftop prism 49 closer to (or further away from) the mirrors 45 and 47 to shorten (or lengthen) the length of the optical delay line 43.

The pump pulse from mirror 41 reflects from mirror 45, translatable rooftop prism 49 and mirror 47 and is transmitted by dichroic beam splitter 39 into the Raman amplifier 21. Thus, the dichroic beam splitter 39 simultaneously reflects the Stokes-shifted light pulse at the Stokes wavelength $\lambda_s$ from the 37 and transmits the pump pulse at the laser wavelength $\lambda_p$ from the mirror 47 into the Raman amplifier 21. Mirrors 37 and 47 and dichroic beamsplitter 39 are adjusted so that the pump light and the signal light overlap in space along the length of Raman amplifier 21.

The translatable rooftop prism 49 can be adjusted in position, as described above, to vary the time of arrival of the pump pulse at the Raman amplifier 21 relative to the signal pulse from the sample 19 in order to form a time-gating operation in the Raman amplifier 21. The relative timing is chosen so as to cause the pump pulse to overlap in time in the Raman amplifier 21 with the signal pulse (which is the image-bearing part of the Stoke-shifted light that was transmitted through the sample 19 and now carries the non-degraded image of the sample 19). In the Raman amplifier 21 the interaction of the pump pulse with the Stokes-shifted light causes that portion of the Stokes-shifted light that overlaps in time with the pump pulse to be amplified. In other words, only the signal pulse will experience gain while the pump pulse is present. The remaining part of the Stokes-shifted light, that arrives at the Raman amplifier 21 after the signal pulse, does not carry an image because of multiple path scattering within the sample 19. This scattered light will not be amplified by the Raman amplifier 21 because, when it does arrive at the Raman amplifier 21, it does not overlap in time with the pump pulse in path 17.

Raman amplifier 21 is comprised of a cell capable of transmitting both the pump pulse and the Stokes-shifted pulse, and it contains a material that produces stimulated Raman amplification of the Stokes-shifted pulse from path 29 when that material is pumped by the pump pulse from path 17. In order to have maximum gain in the Raman amplifier 21, the wavelength of the Stokes-shifted signal light and the wavelength of the pump pulse must be separated by the frequency shift of the Raman material in the Raman amplifier 21. The most reliable way to accomplish this is to fill the Raman generator 23 and the Raman amplifier 21 with the same Raman material (and at the same pressure, if that Raman material is a gas) in order to obtain amplified Stokes signal light from the pump pulse by way of a Raman interaction in the Raman amplifier 21.

The amplification factor or gain of the Raman amplifier 21 is determined by the energy density or power in the pump beam, with a typical value of the order of $10^{10}$. This amplification factor or gain also determines the contrast between the amplified signal pulse image and the delayed scattered light that comes after the amplified image.

Basically, as indicated above, it is the purpose of the Raman amplifier 21 to increase the total energy in the signal pulse to where it is greater than all of the energy contained in the scattered light that follows the signal pulse. As a numerical example, assume that the Raman amplifier 21 has a gain of $10^9$ and that the energy in the scattered light portion of the Stokes light that is transmitted through the sample 19 is $10^8$ greater than the energy in the image-bearing signal pulse. Therefore, of all of the Stokes light that is transmitted through the sample 19, only a very small fraction of such light, corresponding to $10^{-8}$ of it (or one part in $10^8$), carries the image. Obviously, such a low level of light cannot be seen with the human eye or even with the world's most sensitive camera, because it would be swamped by the background scattered light. However, after the Stokes light passes through the gated Raman amplifier 21, the image or signal pulse is amplified by $10^9$), and all of the background scattered light is not amplified at all. As a result, at the output of the Raman amplifier 21 the amplified signal pulse now has 10 times as much energy as all of the unamplified scattered light.

After propagating through the Raman amplifier 21 and being amplified, the amplified Stokes signal pulse at the wavelength $\lambda_s$ is passed through a filter 53, which blocks the pump pulse at the wavelength $\lambda_p$. The amplified Stokes signal pulse then passes through an optical train 55 which relays or reimages the image of the sample 19 from the Raman amplifier 21 to a detector 57. The detector 57 is comprised of a two-dimensional, spatially-resolving detector, such as a charge coupled device (CCD) camera, which is capable of detecting the image of the sample and either displaying it directly or transferring it to suitable recording and processing equipment. The detector 57 must have sufficient sensitivity to respond to the energy of the amplified Stokes signal pulse at the output of the optical train 55, and should be capable of integrating multiple, amplified Stokes signal pulses.

At this point it should be noted that the wavelength of the Stokes light from the Stokes generator 23 and the pulse width of the pump pulse from the laser 11 are determined by the characteristics of the sample 19, and the wavelength of the light pulse from the laser 11 is determined as a function of the type of Stokes material contained in the Raman generator 23.

For example, assume that the sample 19 is live human tissue, such as a human breast. In this case, the Stokes light from the Stokes generator 23 would preferably have a wavelength of about 850 nm. The wavelength of the light pulse from the laser 11 would have to be shorter than the Stokes wavelength of about 850 nm, because the Raman generator 23 produces light that is shifted to a longer wavelength from the wavelength of the light produced by the laser 11 by a frequency corresponding to the Raman shift of the material in the Raman generator 23. If the Raman material in Raman generator 23 was selected to be, for example, hydrogen gas at a preselected pressure, and a Stokes wavelength of 850 nm was desired, the laser 11 would need to produce light at a wavelength of 628 nm.

The width of the pump pulse from the laser 11 is preferably matched to the duration of the signal transmitted through the sample 19. The image transmitted through sample 19 as the signal pulse lasts for a time duration $t_s$, which, for the human breast tissue of this example is estimated to be in the range from 1 to 20 picoseconds. This means that in order for the pump pulse to overlap the image contained in the signal pulse it should preferably have a pulse width of approximately $t_s$. For example, if the image-bearing signal light lasted for 10 picoseconds, the pump pulse should be approximately 10 picoseconds in duration. If, in this example, the pump pulse were 40 picoseconds in duration, however, it would overlap with a part of the Stokes light that contains an image and with a part of the Stokes light that does not contain an image, resulting in a loss of contrast in the amplified image.

Figure 2:
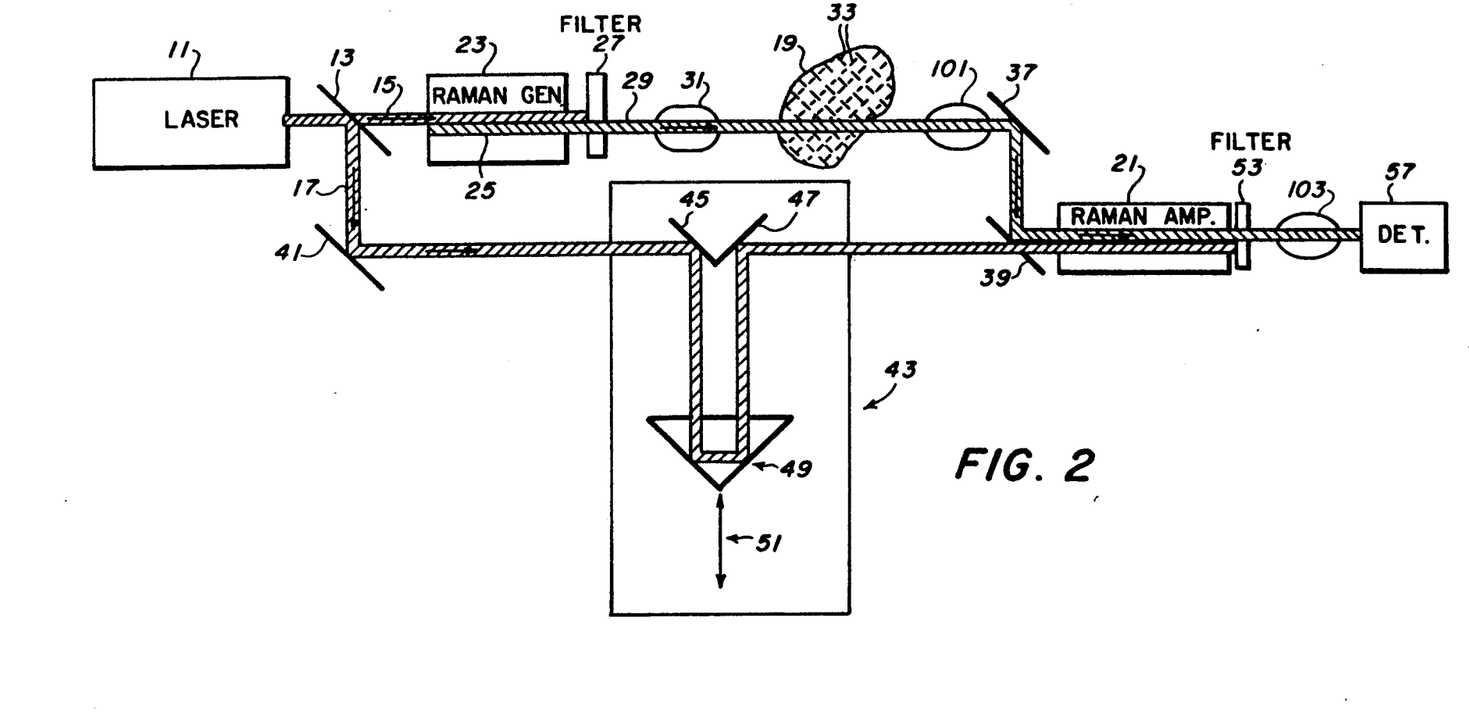
FIG. 2 illustrates a second embodiment of the invention.

Referring now to FIG. 2, a second embodiment of the invention is shown. All of the elements in FIG. 2 are similar in structure and function to the corresponding elements in FIG. 1 having the same reference numerals, except that the optical trains 35 and 55 in FIG. 1 have been replaced by respective optical trains 101 and 103 in FIG. 2. Since all of the elements of FIG. 2 that are common to FIG. 1 have been previously discussed in relation to FIG. 1, these common elements require no further description.

Optical train 101 performs an optical Fourier transform of the Stokes light from the sample 19 and then relays that Fourier transformed Stokes light to the Raman amplifier 21 by way of the mirror 37 and the dichroic beamsplitter 39. The Raman amplifier 21 then amplifies in space the Fourier transformed Stokes light. Since the Raman amplifier 21 amplified a Fourier transform and not an image, optical train 103 takes another Fourier transform of the Fourier transformed image in order to reconstruct the image of the original sample 19, or a plane within that sample 19, at the detector 57. Optical train 103 can be a simple lens or a high quality camera lens (not shown), but its separation from the Raman amplifier 21 and the detector or CCD camera 57 is readjusted so that the function of the optical train 103 is to form a Fourier transform of light from the Raman amplifier 21 rather than forming an image of light from the Raman amplifier 21. The embodiment of FIG. 2 offers an improved signal-to-noise ratio in the amplified image because it does not require exact matching of the structure in the image to the amplifier Fresnel number for minimum noise.

Figure 3:
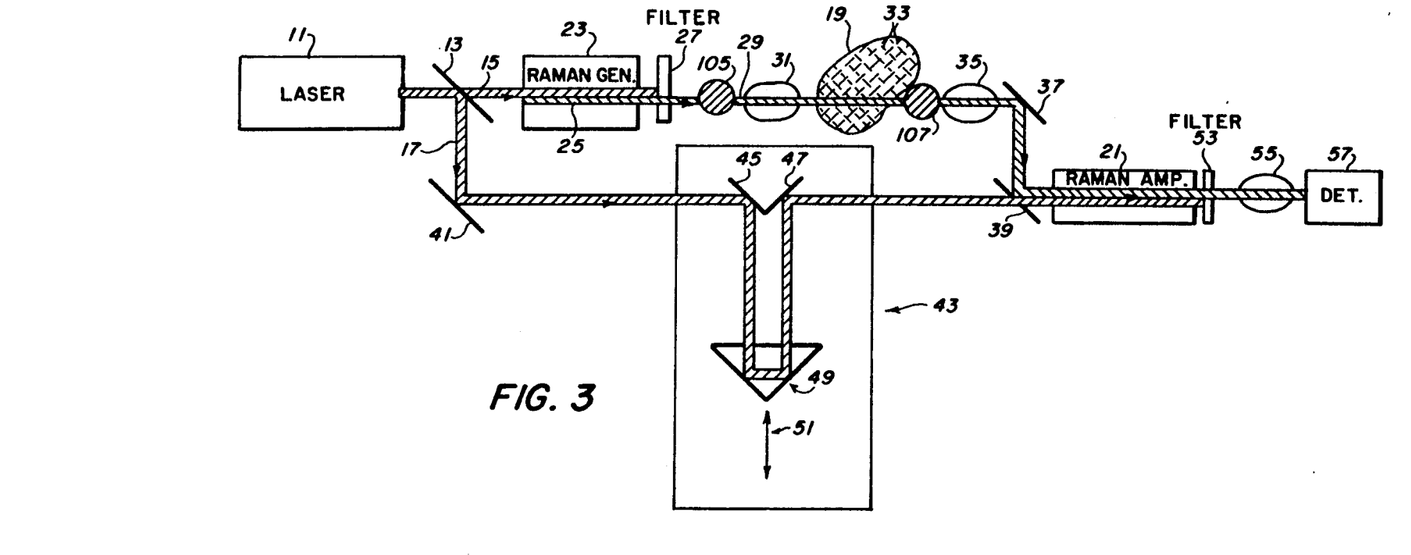
FIG. 3 illustrates a third embodiment of the invention.

Referring now to FIG. 3, a third embodiment of the invention is shown. FIG. 3 contains all of the elements that are shown in FIG. 1, with the same reference numerals. These elements in FIG. 3 are similar in structure and operation to the corresponding elements shown in FIG. 1 and, hence, require no further description. However, FIG. 3 contains two new elements, an expansion dispersive delay line 105 and a compression dispersive delay line 107, which will now be discussed.

The expansion dispersive delay line 105 is inserted in the Stokes-shifted light path 29 between the filter 27 and the optical train 31 to provide a Stokes light pulse that is longer in time and chirped in frequency in order to allow higher energy illumination of the sample 19. On the other hand, the compression dispersive delay line 107 is inserted between the sample 19 and the optical train 35 to compress the pulse that was expanded in the delay line 105 in order to obtain proper time-gating and image resolution of the signal pulse.

The expansion dispersive delay line 105 of FIG. 3 can contain a combination of dispersive elements, such as gratings or prisms and mirrors and lenses, to cause the long wave components of the Stokes light pulse to travel a shorter path than the short wave parts of the Stokes light pulse. An example of a suitable expansion dispersive delay line is shown in FIG. 4.

Figure 4:
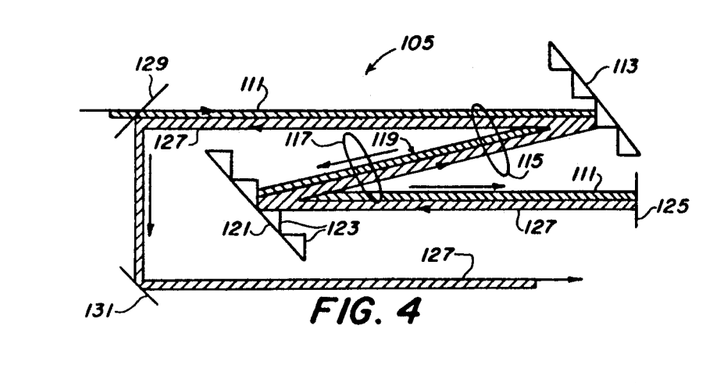
FIG. 4 illustrates in detail the expansion dispersive delay line of FIG. 3.

As shown in FIG. 4, the Stokes light pulse, represented as beam 111, passes from the filter 27 (FIG. 3) and strikes diffraction grating 113, which is oriented to have its grooves vertical, or out of the plane of FIG. 4. Diffraction grating 113 operates to disperse the frequency components of the short Stokes light pulse or beam 111 according to their wavelengths. The frequency dispersed beam 111 then propagates from the diffraction grating 113 through lenses 115 and 117, which are separated from each other by the sum of their focal lengths to form a 1:1 inverting telescope 119. The focal lengths of the lenses 115 and 117 should be equal. The 1:1 inverting telescope 119 operates to reverse the direction of the dispersion from the grating 113 so that the proper arrangement of frequency components will be obtained.

The frequency dispersed beam 111 from the 1:1 inverting telescope 119 then strikes diffraction grating 121, which has vertical grooves 123. The frequency components in this dispersed beam 111 are then parallel to each other, but still dispersed. These parallel, frequency-dispersed components of beam 111 strike a mirror 125, which is positioned to be normal to this beam 111 in the plane of dispersion but slightly tilted off of normal in the vertical direction. As a result, the return beam 127 is reflected back by the mirror 125 along a path that strikes the diffraction grating 121, passes through the lenses 117 and 115 of telescope 119, strikes diffraction grating 113 and continues along a return path which is the path traced by the return beam 127, as shown in FIG. 4. Due to the slight vertical tilt of the mirror 125, the return path of the return beam 127 is offset slightly below the original path of the beam 111. For ease of understanding this description, assume that the original path of the beam 111 lies in the plane of FIG. 4, that the return path of the return beam 127 lies below the plane of FIG. 4 and that a mirror 129 also lies below the plane of FIG. 4.

Upon striking the diffraction grating 113, the return beam 127 is spatially reconstructed and no longer dispersed in space. However, the frequency components in the return beam 127 that are at the red end of the spectrum traveled through the expansion dispersive delay line 105 faster than the frequency components at the blue end of the spectrum. As a result, the Stokes pulse has been chirped from red to blue and has been stretched in time.

At the mirror 129, the spatially reconstructed return beam 127 is below the plane of FIG. 4 and out of the plane of the beam 111. Thus, the return beam 127 strikes the mirror 129 (which also lies below the plane of FIG. 4), is reflected by the mirror 129 away from the incident beam 111, and is reflected from a mirror 131 and out of the expansion dispersive delay line 105 into path 29 (FIG. 3).

This return beam 127 is a long pulse that lies in a different vertical plane than the one in which the short pulse of beam 111 lies. Essentially the short pulse of beam 111 has been stretched in time or duration by the dispersive delay line 105 such that, instead of having a pulse duration of an exemplary 1-20 picoseconds, it now has a pulse duration that is considerably longer than one picosecond. For example, the short pulse of beam 111 can be stretched to have a pulse duration of almost a nanosecond. The exact amount of pulse stretching is determined by the spacing of the grooves on the diffraction gratings 113 and 121 and by the separation of the gratings 113 and 121 from each other.

The stretched Stokes pulse from the expansion dispersive delay line 103 propagates through the optical train 31, which operates to adjust the illumination size and collimation of the Stokes pulse, and then illuminates the sample 19, as discussed before. The Stokes signal light from the sample 19 is substantially compressed to the duration of the original pulse by the compression dispersive delay line 107 in order to obtain proper time-gating and image resolution. The remaining Stokes light will be spread out in time due to multiple path scatter. The compression dispersive delay line 107 is similar to the expansion dispersive delay line 105 described above, except that the sign of the dispersion within delay line 107 is opposite to that in delay line 105. An example of a suitable compression dispersive delay line 107 is shown in FIG. 5.

Figure 5:
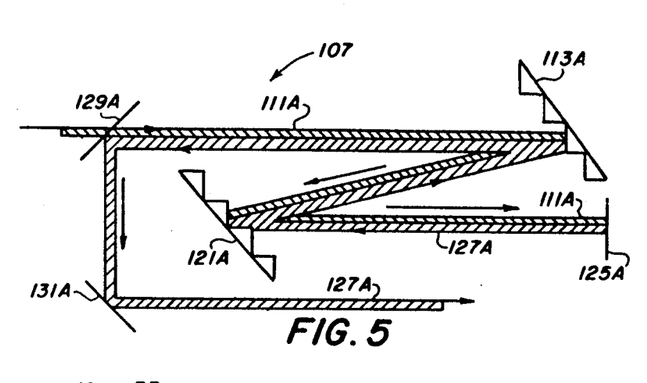
FIG. 5 illustrates in detail the compression dispersive delay line of FIG. 3.

As shown in FIG. 5, the compression dispersive delay line 107 comprises diffraction gratings 113A and 121A and mirrors 125A, 129A and 131A. The elements 113A, 121A, 125A, 129A and 131A of FIG. 5 are respectively similar to the elements 113, 121, 125, 129 and 131 of FIG. 4 in both structure and operation and, hence, require no further description. However, the lenses 115 and 117 of FIG. 4 are not utilized in FIG. 5.

It will be recalled that, in the operation of the expansion dispersive delay line 105 of FIG. 4, the gratings 113 and 121 made the blue light travel faster than the red light, but the lenses 115 and 117 in the telescope 119 inverted the sense of dispersion in the delay line 105, causing the red light to travel faster than the blue light in the delay line 105. Thus, the delay line 105 stretched the short input pulse to produce a long output pulse.

In the operation of the compression dispersive delay line 107 of FIG. 5, the gratings 113A and 121A make the blue light travel faster than the red light. However, since there are no lenses in FIG. 5, there will be no inversion of the sense of dispersion in the delay line 107. As a consequence, the blue light will travel faster than the red light in the delay line 107. Thus, the delay line 107 will compress the long input image-bearing part of the Stokes light from the sample 19 to produce a short signal pulse for proper time-gating and image resolution, as described before. This short signal pulse at the output of the compression dispersive delay line 107 will be reflected by the mirror 131A to the optical train 35 and the operation of the system of FIG. 3 proceeds as previously described in FIG. 1. The non image-bearing component of the Stokes light from sample 19 is stretched out in time due to multiple path scatter and is discriminated against in the Raman amplifier 21, as described before.

The embodiment of FIG. 3 allows greater illumination energy to be used on the sample 19 than is possible with the embodiment of FIG. 1 without increasing the peak intensity. This is a very important consideration when dealing with applications involving living tissue, in which the peak intensity of the illuminating light pulse is limited. It should be understood that modified optical trains 101 and 103 of FIG. 2 can also be utilized in either of the embodiments of FIGS. 1 and 3.

As described above, the invention utilizes stimulated Raman amplification to provide both time-gating and optical amplification. The gate time is determined by the duration of the pump pulse and can be of the order of 1 picosecond or longer. Times of these durations are sufficient to observe images of objects embedded in or viewed through living tissue and other similar dense scattering materials.

The invention has advantages over the previously discussed, prior art techniques. Its gate time is shorter than the electronic gating techniques, allowing imaging through biological tissue. Because of the high gain and low noise level that are possible with the Raman amplifier 21, highly attenuating samples and minimum illumination levels can be used, both important considerations for viewing living tissue.

The high gain allows a contrast level up to $10^{10}$ between the intensity of the amplified image (signal pulse) and the intensity of the delayed scattered light. This provides an improvement over the limitations in contrast of the holographic techniques. The high gain overcomes the limitations present in the Kerr gates due to the transmission losses and in the four-wave mixing techniques due to little or no gain, again allowing minimal illumination levels to be used.

The high sensitivity and two-dimensional imaging capability provide improvements over streak cameras, which have less sensitivity and can provide only a one-dimensional image.

The invention overcomes the limitation of the technique using absorption because it can be used in materials in which absorption is low or non uniform.

The invention also overcomes the limitations of the previously described picosecond time-gated amplifiers by providing increased gain (up to $10^{10}$), improved contrast against the non image-bearing light, reduced fluorescence to eliminate the amplifier generated noise level, and a time bandwidth product of unity, providing the minimum possible noise level to compete with the signal. This last effect is of primary importance in dealing with highly scattering materials, which will have a high extinction coefficient, and materials like living tissue, for which the illumination level is limited.

The invention also provides for the use of chirped pulses for illumination that increases the illumination level that can be used while still maintaining resolution at the level of 10 picoseconds or less.

Therefore, what has been described in various preferred embodiments of the invention is an apparatus and method for the time-gated optical examination of objects that are part of, embedded in or viewed through dense scattering materials using stimulated Raman scattering.

Another embodiment of the invention could use a pulse format for the pump laser that produces a broad bandwidth pulse of relatively long duration, preferably of the order of 1 nsec, but possibly longer. The bandwidth is such that the coherence time of the pulse corresponds to the desired temporal resolution time of the order of 10 psec and possibly less than 1 psec. The temporal structure within the pulse that gives rise to the bandwidth can be either stochastic or coherent, in which case the overall pulse would consist of a series of short pulses of duration comparable to the resolution time. The gating process in the Raman amplifier now occurs because the Raman amplification depends on the correlation between the Stokes light transmitted from the sample and the pump light. Only that portion of the Stokes light that is unscattered or scattered with minimal delay, i.e. the portion that carries the image, will experience maximum gain. Hence the image bearing portion of the Stokes light transmitted through the sample will experience preferential gain in the Raman amplifier over the Stokes light that experiences multiple path scatter. The advantage of this alternative is that more energy can be delivered to the sample than can be used with the short pulse for samples with a limit on peak intensity such as living tissue.

If the image bearing component of the Stokes light that is transmitted through the sample has a substantial component that arises from light that is multiply scattered without significant spatial deviation from its original path, the image bearing component of the Stokes light can have a duration longer than the original Stokes pulse. Under these circumstances it can be advantageous to have the duration of the pump pulse in the Raman amplifier be longer than the original Stokes pulse to overlap in time with the entire image bearing component of the Stokes light. This can be accomplished with the apparatus of FIG. 1 by inserting a narrow band spectral filter in pump beam path 17 to restrict the bandwidth of the pump pulse sufficiently to lengthen its duration by the desired amount. A laser amplifier can then be added if necessary to restore the total pump energy.

It should therefore readily be understood that many modifications and variations of the present invention are possible within the purview of the claimed invention. It is therefore to be understood that, within the scope of the appended claims, the invention may be practiced otherwise than as specifically described.

What is claimed and desired to be secured by Letters Patent of the United States is:

1. An apparatus for examining optically objects that are part of, embedded in, or viewed through a dense scattering material, said apparatus comprising:
   means for producing a first light pulse and a pump light pulse, each of said first and pump light pulses having a preselected pulse width at a preselected pump wavelength;
   means for shifting the pump wavelength of said first light pulse to a preselected Stokes wavelength to form Stokes light;
   means for transmitting said Stokes light through said dense scattering material to obtain Stokes light comprised of a relatively small, image-bearing signal component including unscattered Stokes light or Stokes light with minimal deviation due to scattering, followed in time by a relatively large amount of Stokes light scattered by said material;
   a Raman amplifier, said pump pulse propagating from said producing means to said Raman amplifier during a transit time;
   optical means for transporting said Stokes light from said dense scattering material to said Raman amplifier;
   means disposed between said producing means and said Raman amplifier for varying the transit time of said pump pulse to cause said pump pulse to overlap in time with said signal component of Stokes light at said Raman amplifier, said Raman amplifier only amplifying the signal component of Stokes light that is overlapped by said pump pulse; and
   means for detecting the amplified signal component of Stokes light.

2. The apparatus of claim 1 wherein:
   said shifting means includes a Raman generator and a filter; and
   each of said Raman generator and said Raman amplifier contains a Raman material of the same type as the other one of said Raman generator and said Raman amplifier so that both of said Raman generator and said Raman amplifier have the same Raman shift; and
   said filter blocks said first light pulse at said preselected pump wavelength and only passes therethrough said Stokes light at a wavelength satisfying the relationship $(1/\lambda_p)-(1/\lambda_s)=\nu_o$, where $\nu_o$ is the Raman shift of the Raman material.

3. The apparatus of claim 2 wherein:
   said same Raman material used is both of said Raman generator and said Raman amplifier can be selected from the group consisting of a suitable gas at a predetermined pressure, a suitable liquid, and a suitable solid.

4. The apparatus of claim 2 wherein:
   said same Raman material is a gas selected from the group consisting of hydrogen and methane.

5. The apparatus of claim 1 wherein said transmitting means includes:
   an optical train selected from the group consisting of a lens, a plurality of lenses, a plurality of mirrors, an optical fiber bundle, and a combination thereof.

6. The apparatus of claim 1 including:
   an expansion delay line disposed between said shifting means and said transmitting means for stretching in time the pulse width of the Stokes light in order to allow higher energy illumination of said dense scattering material; and
   a compression delay line disposed between said dense scattering material and said optical means for compressing in time the stretched Stokes light in order to obtain proper time-gating and image resolution of the signal component of the Stokes light in said Raman amplifier.

7. The apparatus of claim 1 wherein said producing means includes:
   a laser for producing a light pulse of said preselected pulse width and at said preselected pump wavelength;
   a mirror operationally coupled to said varying means; and
   a beamsplitter for transmitting a first portion of said light pulse to said shifting means as said first light pulse and reflecting a second portion of said light pulse as said pump pulse, said pump pulse being reflected from said mirror to said varying means.

8. The apparatus of claim 7 wherein:

said shifting means includes a Raman generator and a filter; and each of said Raman generator and said Raman amplifier contains a Raman material of the same type as the other one of said Raman generator and said Raman amplifier so that both of said Raman generator and said Raman amplifier have the same Raman shift and said filter blocks said first light pulse at said preselected pump wavelength and only passes therethrough said Stokes light at a wavelength satisfying the relationship $(1/\lambda_p)-(1/\lambda_s)=\nu_o$, where $\nu_o$ is the Raman shift of the Raman 9. The apparatus of claim 8 wherein said transmitting means includes:

an optical train selected from the group consisting of a lens, a plurality of lenses, a plurality of mirrors, an optical fiber bundle, and a combination thereof.

10. The apparatus of claim 1 wherein said optical means includes:

a mirror for reflecting said Stokes light into an optical path;

a dichroic beamsplitter in said optical path for reflecting said Stokes light to said Raman amplifier;

an optical train transporting said Stokes light from said dense scattering material to said Raman amplifier by way of said mirror and said dichroic beamsplitter; and said dichroic beamsplitter being disposed between said varying means and said Raman amplifier for simultaneously reflecting said Stokes light reflected from said mirror into said Raman amplifier and for transmitting said pump pulse into said Raman amplifier.

11. The apparatus of claim 10 wherein:

said optical train comprises means for relaying the image in the said Stokes signal component to said Raman amplifier by way of said mirror and said dichroic beamsplitter.

12. The apparatus of claim 10 wherein:

said optical train comprises means for performing a Fourier transform of said Stokes optical light from said dense scattering material before relaying said Fourier transformed Stokes light to said Raman amplifier by way of said mirror and said dichroic beamsplitter.

13. The apparatus of claim 12 wherein:

said optical train comprises means for reconstructing the image of the signal component of said Stokes light at said detector.

14. The apparatus of claim 1 wherein said detecting means includes:

a two-dimensional, spatially-resolving detector.

15. The apparatus of claim 14 further including:

a filter disposed between said Raman amplifier and said detector for blocking the pump pulse and passing the amplified signal component of said Stokes light; and an optical train transporting the amplified signal component of said Stokes light from said filter to said detector for detection.

16. The apparatus of claim 15 wherein:

said optical train comprises means for imaging said amplified signal component of said Stokes light onto said detector.

17. The apparatus of claim 1 wherein said detecting means includes:

a charge coupled device camera.

18. A method for examining optically objects that are part of, embedded in, or viewed through dense scattering materials, said method comprising the steps of:

producing a first light pulse and a pump light pulse, each of the first and pump light pulses having a preselected pulse width at a preselected pump wavelength;

shifting the pump wavelength of the first light pulse to a preselected Stokes wavelength to form Stokes light;

transmitting the Stokes light through the dense scattering material to obtain Stokes light comprised of a relatively small, image-bearing signal component including unscattered Stokes light or Stokes light with minimal deviation due to scattering, followed in time by a relatively large amount of Stokes light scattered by said dense scattering material;

transporting the Stokes light from the dense scattering material to a Raman amplifier;

propagating the pump light pulse to the Raman amplifier during a transit time;

varying the transit time of the pump light pulse to cause the pump light pulse to overlap in time with the signal component of Stokes light in the Raman amplifier;

amplifying the signal component of Stokes light in the Raman amplifier during the time that the Stokes light is overlapped by the pump light pulse; and detecting the amplified signal component of Stokes light.

* * * * *